United States Patent [19]

Schneider

[11] Patent Number: 4,832,032

[45] Date of Patent: May 23, 1989

[54] ELECTRICAL APPARATUS PROTECTIVE INTERCONNECT

[75] Inventor: Robert A. Schneider, Del Mar, Calif.

[73] Assignee: La Jolla Technology, Inc., San Diego, Calif.

[21] Appl. No.: 96,240

[22] Filed: Sep. 8, 1987

Related U.S. Application Data

[63] Continuation of Ser. No. 766,209, Aug. 16, 1985, abandoned.

[51] Int. Cl.⁴ .............................................. A61N 1/32
[52] U.S. Cl. ............................. 128/419 R; 128/897; 128/419 PS
[58] Field of Search ................. 128/419 R, 421, 422, 128/783, 419 PC, 419 PS, 736, 1 R, 897; 604/110, 111; 439/259, 296

[56] References Cited

U.S. PATENT DOCUMENTS

| | | | |
|---|---|---|---|
| 474,828 | 5/1892 | Hathaway | 128/733 |
| 2,824,264 | 2/1958 | Anastopoulos | 317/99 |
| 2,871,457 | 1/1959 | Jencks et al. | 339/75 |
| 3,796,221 | 3/1974 | Hagfors | 128/421 |
| 3,835,864 | 9/1974 | Rasor et al. | 128/419 P |
| 4,014,347 | 3/1977 | Halleck et al. | 128/422 |
| 4,084,595 | 4/1978 | Miller | 128/422 |
| 4,121,594 | 10/1978 | Miller et al. | 128/422 |
| 4,141,616 | 2/1979 | Gottlieb | 339/75 M |
| 4,147,171 | 4/1979 | Greene et al. | 128/421 |
| 4,162,536 | 7/1979 | Morley | 364/900 |
| 4,197,944 | 4/1980 | Catlin | 206/306 |
| 4,218,107 | 8/1980 | Wilson | 339/75 P |
| 4,297,530 | 10/1981 | Kessler | 179/2 C |
| 4,387,718 | 6/1983 | Bilitz et al. | 128/419 R |
| 4,406,627 | 9/1983 | Winthrop et al. | 434/219 |
| 4,418,827 | 12/1963 | Butterfield | 215/247 |
| 4,426,122 | 1/1984 | Lainez et al. | 339/45 M |
| 4,466,680 | 8/1984 | Sakai et al. | 339/45 M |
| 4,532,938 | 8/1985 | Carlisle | 128/801 |
| 4,558,914 | 12/1985 | Prager et al. | 339/75 R |
| 4,581,493 | 4/1986 | Gazzo et al. | 179/175.2 C |
| 4,593,365 | 6/1986 | Haley, Jr. et al. | 364/510 |
| 4,597,032 | 6/1986 | Kirby | 362/145 |

FOREIGN PATENT DOCUMENTS 3345444 6/1984 Fed. Rep. of Germany ...... 128/421

OTHER PUBLICATIONS

"Modular Strain Gage Equipment" by Amphenol; Amphenol Engineering News 339-75. M, Summer 1960, p. 575.

"Testing of Electrical Transcutaneous Stimulators for Suppressing Pain" by Carl Mason, Bulletin of Prosthetics Research, Spring 1976, pp. 39-54.

Primary Examiner—Lee S. Cohen
Assistant Examiner—David Shay
Attorney, Agent, or Firm—Robert J. Klepinski; Joseph F. Breimayer

[57] ABSTRACT

An electrical apparatus protective interconnect module including a casing having therein a chamber at one end and a socket at the other end for receiving within the socket an electrical apparatus having controls. A power supply is contained within the chamber and provide power to the electrical apparatus received within the socket. Connectors are located between the chamber and the socket for coupling the power supply to the electrical apparatus received within the socket. The casing encloses and restricts access to predetermined controls of the electrical apparatus received within the socket. The module further comprises externally accessible outputs for coupling an electrical signal output of the electrical apparatus, received within the socket, from the casing to external electrodes.

3 Claims, 2 Drawing Sheets

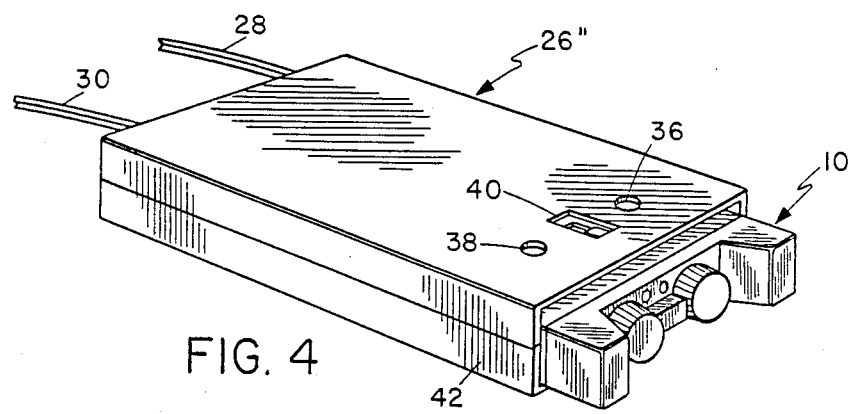
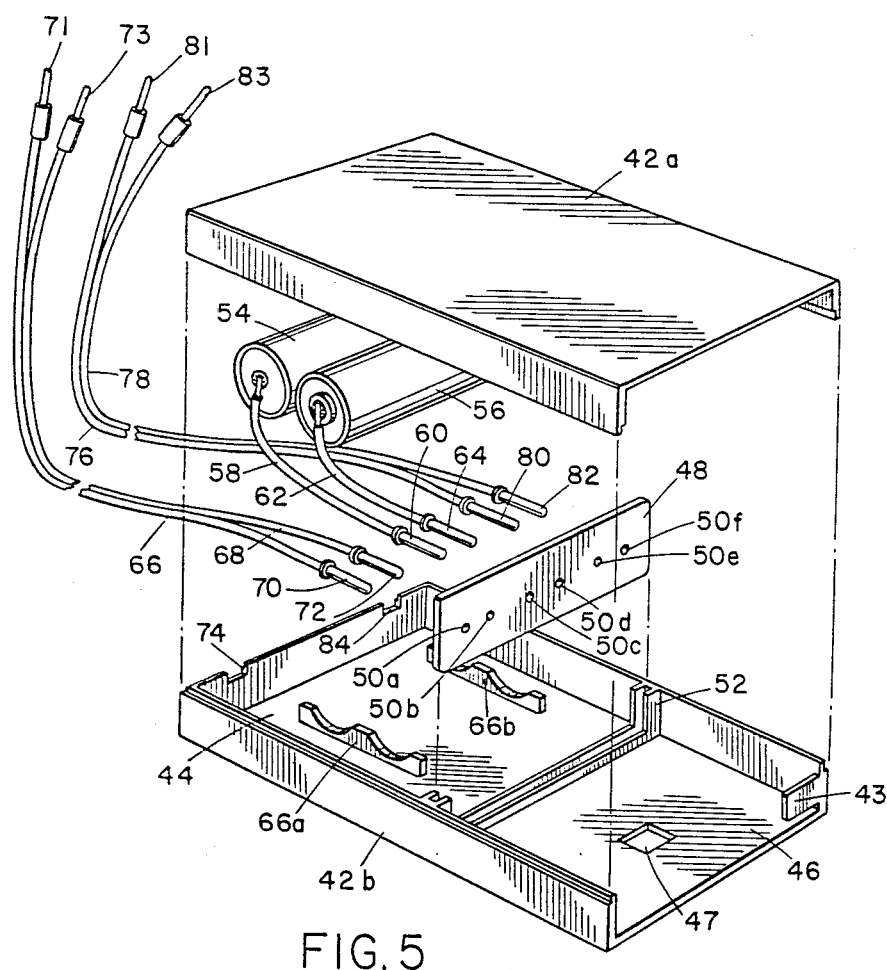

ELECTRICAL APPARATUS PROTECTIVE INTERCONNECT

This is a continuation of co-pending application Ser. No. 766,209 filed on Aug. 16, 1985, now abandoned.

BACKGROUND OF THE INVENTION

I. Field of Invention

The present invention relates to electrical apparatus protective interconnect modules. More specifically, the present invention relates to a novel disposable post-operative transcutaneous electrical nerve stimulator (TENS) protective interconnect module which provides battery power to and treatment signal output from a TENS unit while providing limited access to certain controls located on the TENS unit.

II. Background of the Art

Transcutaneous electrical nerve stimulator (TENS) units are used to generate electrical stimulation signals which are applied to the body of a patient to alleviate pain. Most recently, the use of a TENS unit has been viewed as a viable alternative for reducing pain a patient may experience in a post-operative environment. The use of a TENS unit in the post-operative environment has significant advantages in reducing pain as compared to narcotic drugs which have associated physiological side effects.

Previously, TENS units have included certain controls which the operator/patient may adjust. An example of such controls may be on/off, pulse amplitude, pulse width, pulse rate, and various forms of pulse modulation. It is difficult for someone less than a trained operator, skilled clinician, or repetitive user to properly adjust the controls to provide the most efficacious output signals. Therefore, in applications such as in the post-operative where typically a patient has had only limited exposure to TENS, it is desirable that the controls be preset to provide the preferred output signal for the particular application. Another consideration in the use of a TENS unit in the post-operative environment is the susceptibility of the controls to accidental adjustment or tampering by the patient. In a preferred mode, preset controls are desired which are inaccessable to the patient but which are accessable for adjustment by authorized and properly trained personnel.

Generally, TENS units have employed batteries typically four individual cells, a custom battery pack comprised of four cells or a 9 volt battery which are integrated within the TENS unit itself. Integration within the TENS unit itself may result in battery connections being affected by external contaminants. Contamination of battery contacts due to battery leakage, contact spring material oxidation, or too low of contact pressure on the battery springs due to use may result in intermittent or permanent device failure.

When using non-rechargeable disposable batteries, the hospital staff cannot easily distinguish new from partially discharged batteries and may inadvertently use partially discharged batteries on a new patient. With TENS units using multiple standard commercial cells, e.g. 4-AA cells, problems such as installation of batteries with incorrect polarization or theft of battery inventories may occur. With a conventional 9 volt battery, the installation factors are not a problem. However, limited power capacity restricts the usefullness of this type of battery. Also, due to the popularity of this type of battery, battery theft reduces the desirability of usage of this battery type.

When using rechargeable batteries, the hospital staff must either test or replace and recharge battery packs that are questionable prior to usage. Rechargeable battery packs would need to be recharged by hospital personnel prior to usage thereby requiring additional hospital staff time and facilities for this task. Efforts associated with both the monitoring of rechargeable battery status or the recharging of batteries can result in inefficient use of hospital personnel.

Other factors which affect the use of TENS unit in post-operative situation is that the TENS unit, battery pack and lead wires may be contaminated by liquid spills or other external contaminants. Even if no contamination were to occur by usage with a patient, typical hospital procedures would include cleaning of the device before use with another patient. Nevertheless, under any circumstances the unit and lead wires would have to be cleaned before usage with another patient. Again, a cleaning operation would require additional hospital staff resources.

Another disadvantage of a conventional TENS unit in the post-operative environment are the long term use related failures. Such failures appear, for example, in the TENS unit's lead wires which couple the TENS unit's electrical output signal to the electrodes. The leads may experience connector/lead stress fatigue or lead discontinuity due to conductor breakage, over long term use. In a re-use situation leads may need to be tested to ensure operability, thus requiring additional hospital staff resources.

It is therefore an object of the present invention to provide a new and improved electrical apparatus protective interconnect module which protects the electrical apparatus from external factors, such as contaminants and control tampering.

It is a further object of the present invention to provide a low cost, highly reliable, disposable TENS protective interconnect module, for use with a post-operative TENS unit, which provides reduced maintenance in the post-operative environment.

It is yet another object of the present invention to provide a TENS protective interconnect module wherein substantial portions of the protective interconnect module which come in contact with a patient are disposable.

SUMMARY OF THE INVENTION

The present invention provides a new and improved protective interconnect module for a TENS unit for utilization in the post-operative environment. The present invention is characterized by a highly reliable protective interconnect module that is disposable and also serves to protect a TENS unit from external contaminants. Since the protective interconnect module includes electrode lead wires and is disposable, it eliminates long term usage failures that are related to a TENS unit's electrode leads. Also eliminated are electronic failures due to battery connection problems caused by battery leakage corrosion, oxidation, contaminants and weak battery contact springs.

The protective interconnect module of the present invention prevents patient tampering and unskilled operator adjustments by limiting access to certain controls on a coupled TENS unit. As a disposable unit, the protective interconnect module eliminates the need to test or recharge batteries since it is disposed of after each patient use. Another advantage of the protective interconnect module is that since it is disposed of after each use, patient-to-patient contamination is reduced. This is a result of the TENS unit being protected within the confines of the protective interconnect module which is disposed of after patient usage.

In accordance with the present invention, in one specific application of the protective interconnect module a TENS protective interconnect module is disclosed which includes a casing having therein a chamber at one end and a socket at the other end for receiving within the socket a TENS unit having controls. Battery means are contained within the chamber for providing power to the TENS unit received within the socket and connection means are located between the chamber and socket for coupling the battery means to the TENS unit received within the socket. The casing of the protective interconnect module encloses and restricts access to predetermined controls of the TENS unit received within the socket. The protective interconnect module further includes externally accessible output means for coupling the output of a TENS unit, received within the socket, from the casing to external electrodes.

BRIEF DESCRIPTION OF THE DRAWINGS

These features, objects, and advantage of the present invention will be more fully apparent from the detailed descriptions set forth below when taken in conjunction with the drawings in which like reference characters correspond throughout and wherein:

FIG. 4 is a perspective view of the TENS unit of FIG. 1 inserted in the protective interconnect module; and FIG. 5 is an exploded perspective view of the protective interconnect module.

DETAILED DESCRIPTION OF THE PREFERRED EMBODIMENTS

Figure 1:
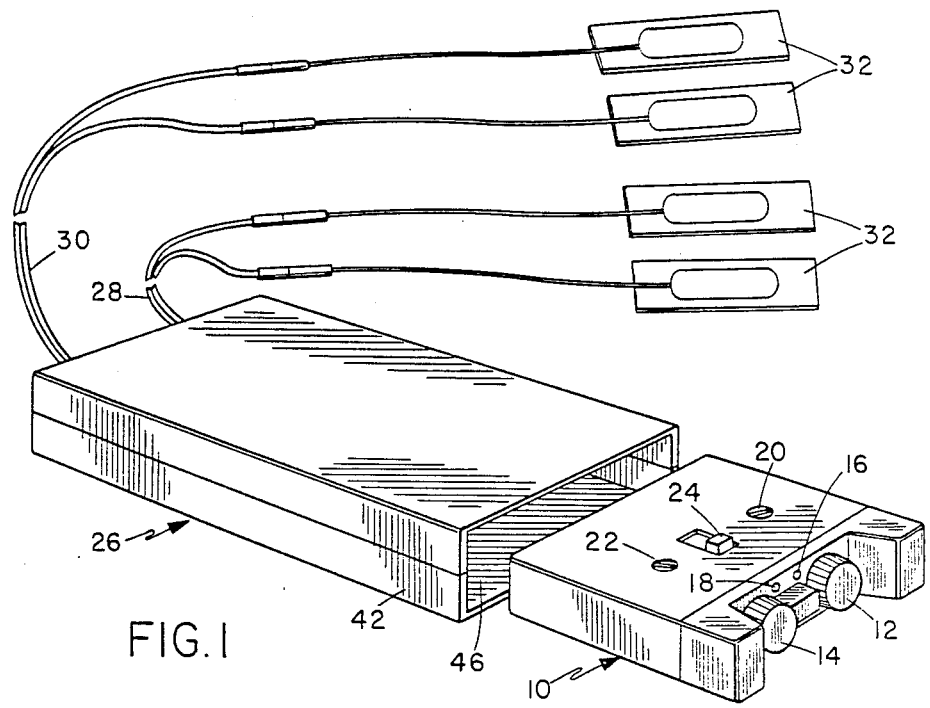
FIG. 1 is a perspective view of the TENS unit with the protective interconnect module and electrode assembly.

FIG. 1 illustrates a dual channel post-operative TENS unit 10 having separate channel amplitude controls. At one end of TENS unit 10 are a pair of amplitude controls 12 and 14 each associated with a different channel. Each amplitude control also functions as an on/off switch for the associated channel. At the same end of the TENS unit as amplitude controls 12 and 14 are on/off indicator 16 and low battery indicator 18. On the side of TENS unit 10 is a pulse width control 20 and pulse rate control 22. Also on the side of TENS unit 10 is a signal selector switch 24 which permits the operator to select between output pulse modes, i.e., normal or modulation modes.

TENS unit 10 is inserted within protective interconnect module 26. Protective interconnect module 26 includes a substantially rectangular casing 42 which is open at one end so as to provide a socket 46 for receiving TENS Unit 10. When the TENS unit 10 is received within protective interconnect module 26 it is coupled therein to a battery means which provides power to TENS unit 10. In addition, protective interconnect module 26 couples the output of each channel of TENS unit 10 via a connection means, including lead pairs 28 and 30, to electrodes 32.

Figure 2:
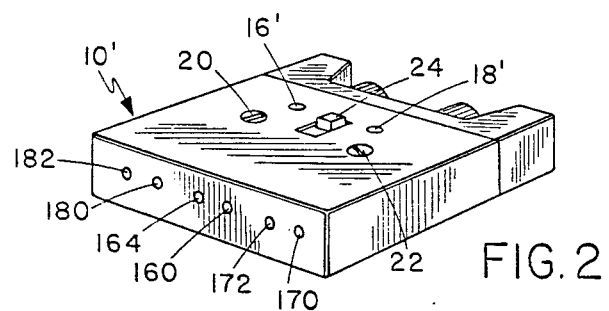
FIG. 2 is a perspective view, from the rear, of a slightly modified TENS unit.
Figure 3:
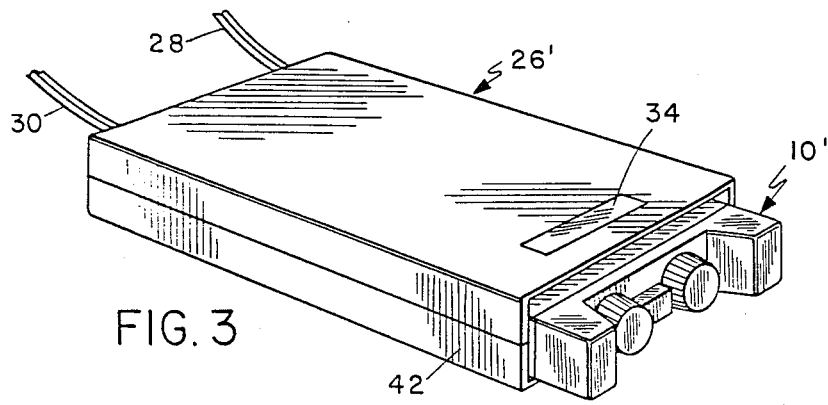
FIG. 3 is a perspective view of the TENS unit of FIG. 2 inserted in the protective interconnect module.

When the TENS unit 10 is inserted within protective interconnect module 26, certain controls, such as pulse width control 20, pulse rate control 22, and selector switch 24, are enclosed by the walls of case 42 thereby restricting access to these controls. In an alternate embodiment of an interconnect module as illustrated in FIG. 3, protective interconnect module 26' includes a transparent or translucent viewing window 34 in a side of case 42 so as to permit viewing of on/off indicator 16' and low battery indicator 18' which are mounted on the side of the TENS unit 10'. On/off indicator 16' and low battery indicator 18' are located on the side of TENS unit 10' adjacent the pulse mode controls as illustrated in FIG. 2. It is envisioned that viewing window 34 may be expanded to permit viewing of the additional controls or indicators mounted on the side of TENS unit 10'.

FIG. 4 illustrates yet another embodiment of the present invention wherein TENS unit 10 is inserted within protective interconnect module 26''. Protective interconnect module 26'' includes openings 36, 38 and 40 for limited access to pulse width control 20, pulse rate control 22 and selector switch 24. These controls may be adjusted by a special tool or other means adapted for adjusting the particular control.

In FIG. 5, protective interconnect module 26 is comprised of casing 42 formed from two mating casing halves 42a and 42b. When casing halves 42a and 42b are coupled together they form at one end a chamber 44 and a socket 46 at the other end for receiving within socket 46 a TENS unit. Means are included so as to provide a visual indication of whether the TENS unit has been plugged into the protective interconnect module. An example of such an indication means is tab 43 molded onto one of casing halves 42a and 42b. Tab 43 breaks away from the casing half or folds over when a TENS unit is inserted into socket 46. Tab 43 alerts the user to the fact that the protective interconnect module is new or used so as to avoid re-use of a used protective interconnect module. Casing half 42b may also contain a window 47 made of an optically transparent material such as clear plastic. Window 47 will permit optical transmission of a trigger pulse signal from a TENS unit to an external accessory, such as an ECG filter.

Another use of window 47 would be to permit the transmission of various TENS unit operating status signals to equipment external to the protective interconnect module. Such status signals may include low battery condition, open circuit condition and other signals. Disposed between chamber 44 and socket 46 is terminal board 48 which is retained therein by channel or guide 52. A guide 52 is molded within casing halves 42a and 42b. Casing 42 is formed from a durable lightweight material such as a high-impact plastic which can be easily molded. Terminal board 48 is formed from an electrically insulating material such as fiber board or plastic. Terminal board 48 includes a sequence of spaced apart holes 50a–50f in which pin connectors are mounted.

Battery means are contained within chamber 44 for providing power to a TENS unit received within socket 46. In one embodiment of the invention, a pair of 1.5 volts "C" size alkaline batteries are series connected by spot welding a bus bar (not shown) between the positive terminal of battery 54 to the negative terminal battery 56. Spot welding of battery terminals to the bus bar and terminal leads increses contact reliability over spring contacts and is readily adaptable for automated assembly of the protective interconnect module. Battery lead 58 is welded at one end to the negative terminal of battery 54 and is coupled to pin connector 60 at the other end. Pin connector 60 is mounted in terminal board 48 in hole 50c so as to project therethrough into socket 46 for engaging with a TENS pin socket 160. Similarly, battery lead 62 is welded at one end to the positive terminal of battery 56 while at the other end is connected to pin connector 64. Pin connector 64 is mounted in opening 50d of terminal board 48 and projects therethrough into socket 46 for engaging pin socket 164. In the preferred embodiment, all pin connectors associated with the batteries are large area, high pressure, self-wiping connectors. Batteries 54 and 56 are retained from movement within chamber 44 by mounting on guides 66a and 66b and/or by means such as encapsulation.

Output means are included for coupling the output of a TENS unit received within socket 46 to externally located electrodes. For a single channel TENS output, leads 66 and 68 are respectively coupled to pin connectors 70 and 72. Pin connectors 70 and 72 are respectively mounted in holes 50a and 50b of terminal board 48. Pin connectors 70 and 72 project through terminal board 48 into socket 46 so as to respectively engage with TENS pin sockets 170 and 172. Leads 66 and 68 extend through chamber 44 and external to casing 42 through an opening 74 which has provisions for strain relief.

Similarly, the output of a second TENS channel may be provided on leads 76 and 78 which are respectively coupled to pin connectors 80 and 82. Pin connectors 80 and 82 are respectively mounted on holes 50e and 50f of terminal board 48. Pin connectors 80 and 82 project through terminal board 48 into socket 46 so as to engage with TENS pin sockets 180 and 182. Leads 76 and 78 extend through chamber 44 and external to casing 42 through hole 84 which has provisions for strain relief.

Leads 66 and 68 respectively include connectors 71 and 73 at ends opposite connector 70 and 72. Similarly, leads 76 and 78 include connectors 81 and 83 at ends opposite pin connectors 80 and 82. Pin connectors 71, 73, 81 and 83 are used for mating with electrodes connectors such as electrodes 32 as illustrated in FIG. 1. Leads 66, 68, 76, 78 are of a sufficient length to reach the electrode connectors. Post-operative electrode leads are typically of a length sufficient to reach the TENS unit lead connectors which are located outside of the area kept sterile during a surgical procedure.

Holes 50a–50f in terminal board 48 are each held to close dimensional tolerances with relation to each other. Hole spacing tolerance control is necessary for proper alignment of the pin connectors when coupling with respective pin sockets of a TENS unit. Terminal board 48 is permitted minor freedom of movement in all directions within guide 52 so as to allow for less tolerance control in the molding of casing 42. More importantly, side to side movement is permitted which allows pin alignment when a TENS unit is inserted into the protective interconnect module.

Strain relief means may be included and mounted at hole 74 and 84 so as to prevent accidental removal of electrode leads 66, 68, 76, and 78 from the protective interconnect module. In an alternative embodiment, means are included for decoupling the electrode leads 66, 68, 76 and 78 from the casing 42. One such example of a decoupling means is a quick-disconnect lead clamp which forces connection prongs through the lead wires upon clamping. This decoupler permits selective removal of leads that will not be needed, such as when only single channel output is required.

The output of the TENS unit is coupled through leads 66, 68, 76, and 78 which are integrated within a disposable unit. Therefore, long-term connector failures associated with reusable leads extending from a TENS unit are eliminated. Furthermore, since the protective interconnect module of the present invention is a disposable unit with a limited lifetime, it would not be necessary to clean the module after each use. The disposable aspect of the invention results in a reduction in equipment cleaning costs and long term maintenance. Due to the limited period of use of the protective interconnect module of the present invention, reliability failures such as mechanical failures of wires and connectors is substantially reduced. Another aspect of the invention is that the batteries are welded together within a sealed chamber and are protected from contaminants such as liquid spills. Furthermore, as a result of the batteries being physically isolated from the electronics, electronic failures due to battery leakage are eliminated.

Although the preferred embodiment of the protective interconnect module of the present invention has been described with reference to using a pair of "C" cell batteries, other cell types may be utilized. With "C" cell alkaline batteries, battery life in a dual channel TENS unit is typically, under worst case conditions 82 hours with full output power from both channels and 150 hours for a single channel at full power output. Battery type selection permits the TENS protective interconnect module to be tailored to achieve different levels of module life.

The protective interconnect module of the present invention permits hospital personnel to use a TENS unit having pre-set controls that is contained within the disposable protective interconnect module. More specifically the protective interconnect module casing protects the TENS unit from spills while restricting access to the pre-set controls.

The previous description of the preferred embodiments are provided to enable any person skilled in the art to make or use the present invention. Various modifications to these embodiments will be readily apparent to those skilled in the art, and the generic principles defined herein may be applied to other embodiments which may be used for electrical apparatus other than TENS units in other application, for TENS unit purposes or various other embodiments without the use of the invented faculty. Thus, the present invention is not intended to be limited to the embodiment shown herein, but is to be accorded the widest scope consistent with the principles and novel features disclosed herein.

What is claimed is:

1. A disposable module for use in conjunction with a TENS unit comprising:
    a casing having chamber means for removably receiving and substantially enclosing the TENS unit;
    a battery mounted in the casing for providing electrical power;
    battery connector means electrically coupled to the battery for providing power to the TENS unit when mounted in the chamber means;
    a pair of output leads mounted in the casing and extending outside the casing having sufficient length to extend to a stimulation site for connection to medical electrodes; and lead connector means, electrically connected to the output leads, for electrically connecting output leads to circuitry in the TENS unit.

2. A medical electrical stimulator comprising:

a reusable TENS unit for generating electrical pulses for patient stimulation;

connector means on the TENS unit for connecting to battery power and to output means for outputting a TENS signal;

a disposable module comprising:

a casing provided with a socket means for removably receiving and substantially enclosing the TENS unit;

terminal means for connecting to the connector means of the TENS unit when the TENS unit is mounted in the socket means and enclosed by the casing;

a battery mounted in the casing and electrically connected to the terminal means for electrical connection to the connector means of the TENS unit; and a pair of lead wires mounted in the casing and electrically connected to the terminal means for connection to the connector means of the TENS unit and extending outside of the casing for connection to patient electrodes.

3. The stimulator of claim 2 wherein the connector means includes a pair of battery pin sockets and a pair of lead pin sockets; and the terminal means includes a pair of battery pin connectors and a pair of lead pin connectors arranged such that when the TENS unit is inserted in the socket means in the casing, the battery pin connectors are inserted in and electrically connected to the battery pin sockets and the lead pin connectors are inserted in and electrically connected to the lead pin sockets so that battery power is provided to the TENS unit and stimulation pulses are provided from the TENS unit to the lead wires.

* * * * *